(12) United States Patent
Coates

(10) Patent No.: US 8,474,467 B2
(45) Date of Patent: Jul. 2, 2013

(54) TEETH CLEANING APPARATUS

(76) Inventor: Eric Leonard Coates, Wollstonecraft (AU)

( * ) Notice: Subject to any disclaimer, the term of this patent is extended or adjusted under 35 U.S.C. 154(b) by 1129 days.

(21) Appl. No.: 12/093,103

(22) PCT Filed: Sep. 27, 2006

(86) PCT No.: PCT/AU2006/001411
§ 371 (c)(1),
(2), (4) Date: May 8, 2008

(87) PCT Pub. No.: WO2007/056793
PCT Pub. Date: May 24, 2007

(65) Prior Publication Data
US 2008/0254408 A1  Oct. 16, 2008

(30) Foreign Application Priority Data

Nov. 15, 2005  (AU) ................................ 2005906306
Jun. 13, 2006  (AU) ................................ 2006903177

(51) Int. Cl.
*A61C 15/00* (2006.01)
(52) U.S. Cl.
USPC ........................... 132/322; 132/321; 433/216
(58) Field of Classification Search
USPC ................. 433/118–122, 103, 105, 114, 124, 433/127, 131, 91–92; 132/308–309, 321–329; 15/206, 207.2, 167.1, 22.1, 22.2
See application file for complete search history.

(56) References Cited

U.S. PATENT DOCUMENTS

| | | | | |
|---|---|---|---|---|
| 4,058,896 | A | * | 11/1977 | Moore ............................ 433/91 |
| 4,169,984 | A | * | 10/1979 | Parisi ....................... 310/323.18 |
| 4,735,200 | A | * | 4/1988 | Westerman ................... 601/162 |
| 5,000,684 | A | | 3/1991 | Odrich |
| 5,429,145 | A | * | 7/1995 | Bral .............................. 132/323 |
| 5,496,218 | A | * | 3/1996 | Brahler ......................... 464/182 |
| 5,613,258 | A | * | 3/1997 | Hilfinger et al. .............. 15/22.1 |
| 5,827,064 | A | | 10/1998 | Bock |
| 6,050,818 | A | * | 4/2000 | Boland et al. ................ 433/118 |
| 6,102,700 | A | * | 8/2000 | Haczek et al. ............... 433/118 |
| 6,447,293 | B1 | | 9/2002 | Sokol et al. |
| 6,602,071 | B1 | * | 8/2003 | Ellion et al. ................... 433/80 |
| 2004/0214135 | A1 | * | 10/2004 | Ruddle ......................... 433/102 |
| 2005/0037316 | A1 | | 2/2005 | Sholder |
| 2006/0174910 | A1 | * | 8/2006 | Coopersmith ................ 132/321 |

FOREIGN PATENT DOCUMENTS

DE  4029050 A1  3/1992

* cited by examiner

*Primary Examiner* — Yogesh Patel
(74) *Attorney, Agent, or Firm* — Brooks Kushman P.C.

(57) ABSTRACT

Teeth cleaning apparatus comprises a cylindrical cleaning implement. The cleaning implement includes a resilient support shaft and an engagement thread and is drivingly rotatable. The implement is so configured that, when presented between a pair of adjacent teeth, a rotating implement threads itself into the interproximal space and extracts interproximal debris.

15 Claims, 4 Drawing Sheets

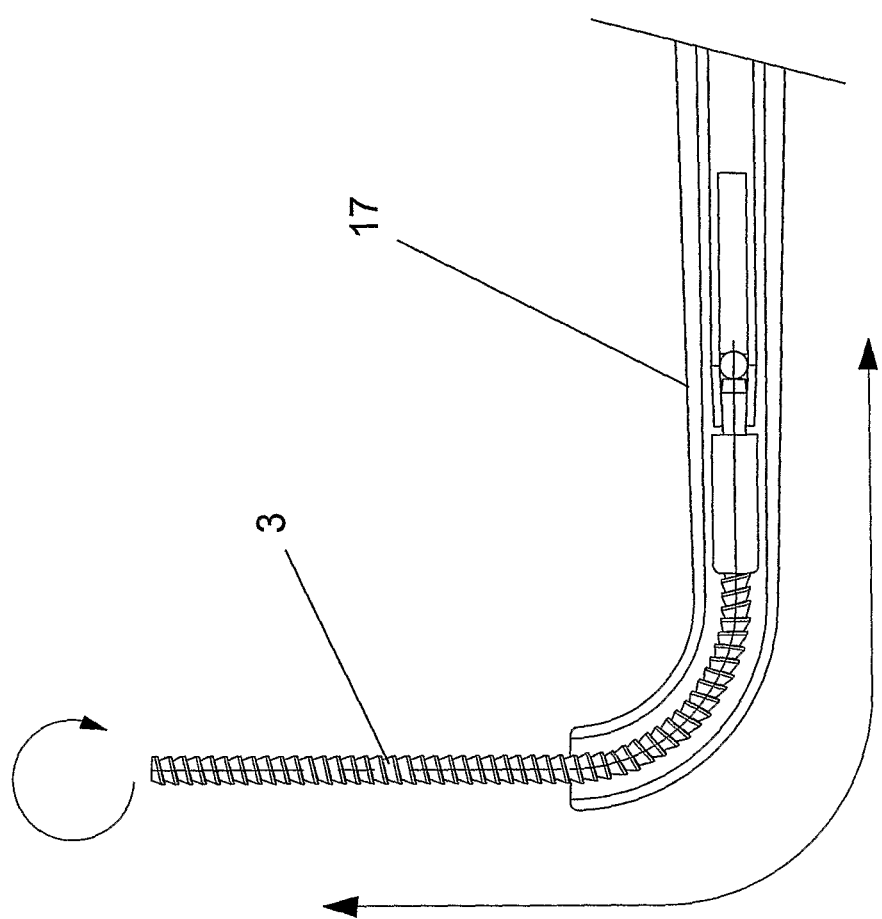

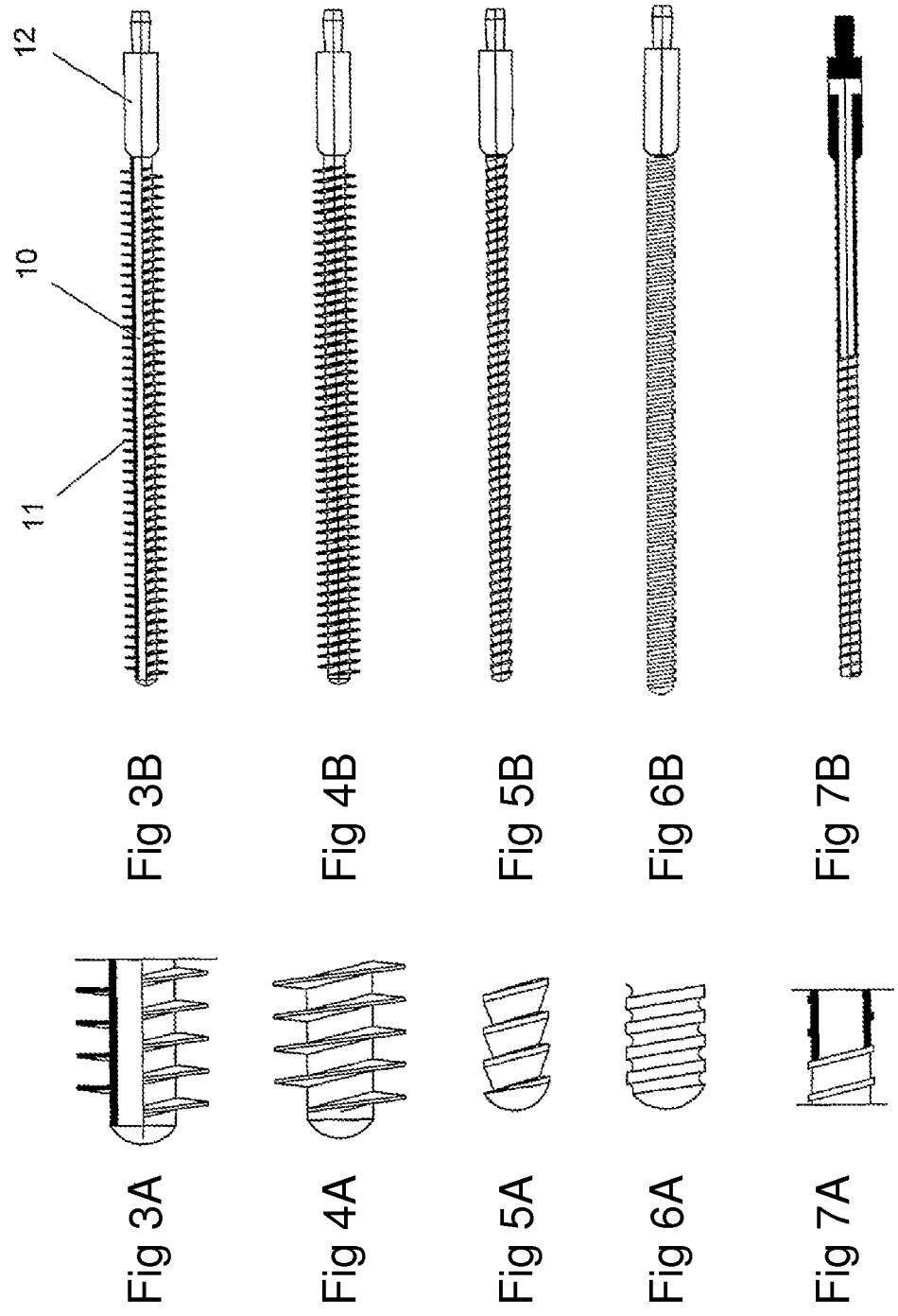

TEETH CLEANING APPARATUS

TECHNICAL FIELD

The invention described herein relates to an implement and an apparatus for interproximal cleaning and removal of biofilm from user's teeth.

BACKGROUND OF THE INVENTION

The conventional tools for Interproximal cleaning and biofilm removal include floss, ribbon and interproximal brushes. All these tools, however, tend to push at least some of the debris through the small gap at the base of the teeth and down below the gum. In addition, the use of these tools is somewhat inconvenient and less dextrous users, such as those with Multiple Sclerosis or arthritis, or users with large hands, find such a use difficult.

There have also been previous attempts to automate the interproximal cleaning. For example, both U.S. Pat. No. 6,102,700, by Haczek et al., and U.S. Pat. No. 6,050,818, by Boland et al., disclose electrical power dental cleaning devices employing a cleaning implement rotated around a longitudinal axis. Various features of the driving mechanisms of such an arrangement are discussed. Document US 2005/0037316, on the other hand, discloses a cleaning implement, which is driven by sonic waves.

One of the problems is that the cleaning implement used in these automated systems tends to push debris below the gum. Another problem relates to the fact that a very fine resilient probe, less than 0.5 mm diameter, is required to access very small crevices. Such a fine probe easily crumples or collapses when compressed during insertion. This imposes stringent requirements on the strength and the hardness of the cleaning implement. On the other hand, the implement needs to also be sufficiently flexible so as to prevent damage to the gum tissues of a user. Previous attempts have found it difficult to reconcile these contradicting requirements.

Accordingly, it is preferable for an automated arrangement to be designed, which is reliable and provides efficient interproximal cleaning.

SUMMARY OF THE INVENTION

According to one embodiment of the invention, there is provided a teeth cleaning apparatus comprising a cylindrical cleaning implement, wherein the cleaning implement is drivingly rotatable and comprises a resilient support shaft and an engagement thread configured so that, when presented between a pair of adjacent teeth, the rotating cleaning implement threads itself into the interproximal space and extracts interproximal debris.

Preferably, the apparatus further comprises an elongate housing and an electronic driving mechanism disposed in the housing, wherein the cylindrical cleaning implement is, at least partially, laterally supported within the housing, drivingly rotated by the driving mechanism and axially movable between a retracted configuration, wherein the implement is enclosed in the housing, and an operative configuration, wherein the implement extends, at least partially, outside the housing.

Even more preferably, the engagement thread comprises substantially continuous helical thread with a small helix angle with respect to a plane transverse to the axis of the implement. The helix angle is preferably less than 60 degrees or, even more preferably, less than 20 degrees.

In some embodiments, the apparatus also comprises a pump arranged to provide vacuum, the vacuum being applied in the interproximal space adjacent the cleaning implement to facilitate extraction of debris, the extracted debris being then flushed out of the cleaning apparatus or transferred to a dedicated storage space.

Preferably, the housing comprises a rear portion, including the driving mechanism, and a front portion, including an elongate tubular support portion for housing and laterally supporting the cleaning implement, the rear and the front portions being axially movable with respect to each other, wherein moving the front portion towards the rear portion effects the operative configuration of the cleaning implement, and moving of the front portion away from the rear portion effects the retracted configuration of the cleaning implement.

Also preferably, the tubular support portion includes a curved portion to allow the tip of the implement to be conveniently introduced into the interproximal space under an angle with respect to the axis of the cleaning apparatus. The angle of the curved portion is preferably 90 degrees.

Preferably, the front portion is resiliently biased away from the rear portion, the arrangement being such that, pushing the front portion towards the rear portion effects the operative configuration of the cleaning implement, while releasing of the front portion allows the bias to bring the implement into the retracted configuration.

Preferably, the shaft of the cleaning implement is hollow so as to facilitate applying of vacuum and extracting interproximal debris through at least one opening in the shaft.

In some embodiments, the driving mechanism comprises:
  an electric motor for drivingly rotating the cleaning implement in at least one direction;
  a first drive shaft arranged for engaging with the cleaning implement and the motor so as to transfer the rotational movement from the motor to the implement;
  a clutch arranged between the motor and the first drive shaft, the clutch being arranged to facilitate disengagement of the first drive shaft from the motor in case of jamming of the implement; and
  a second shaft arranged for engaging the electric motor to the clutch;
  wherein the second shaft is drivingly engaged with the pump.

In a similar aspect of the invention, there is provided a teeth cleaning apparatus comprising:
  an elongate housing;
  a driving mechanism disposed in the housing; and
  a cylindrical cleaning implement being, at least partially, laterally supported within the housing, the cleaning implement being drivingly rotatable by the driving mechanism and being axially movable between a retracted configuration, wherein the implement is enclosed in the housing, and an operative configuration, wherein the implement extends, at least partially, outside the housing;
  wherein the cleaning implement comprises a resilient support shaft and an engagement thread configured so that, when presented between a pair of adjacent teeth, the rotating cleaning implement threads itself into the interproximal space and extracts interproximal debris.

In some embodiments in the teeth cleaning apparatus of the above aspects, the thread is flexible. Preferably, the cleaning implement of the teeth cleaning apparatus of the above aspects is of integral structure.

In another aspect of the invention, there is provided an implement for use with the teeth cleaning apparatus of the previous aspects of the invention.

BRIEF DESCRIPTION OF THE DRAWINGS

A preferred embodiment of the invention will now be described by way of example only and with reference to the accompanying drawings wherein:

FIG. 2 is a schematic cross-sectional view of a front section of the apparatus of FIG. 1, including the cleaning implement.

FIG. 3A to FIG. 7B show various embodiments of the cleaning implement of the apparatus of FIG. 1.

PREFERRED EMBODIMENT OF THE INVENTION

Figure 1:
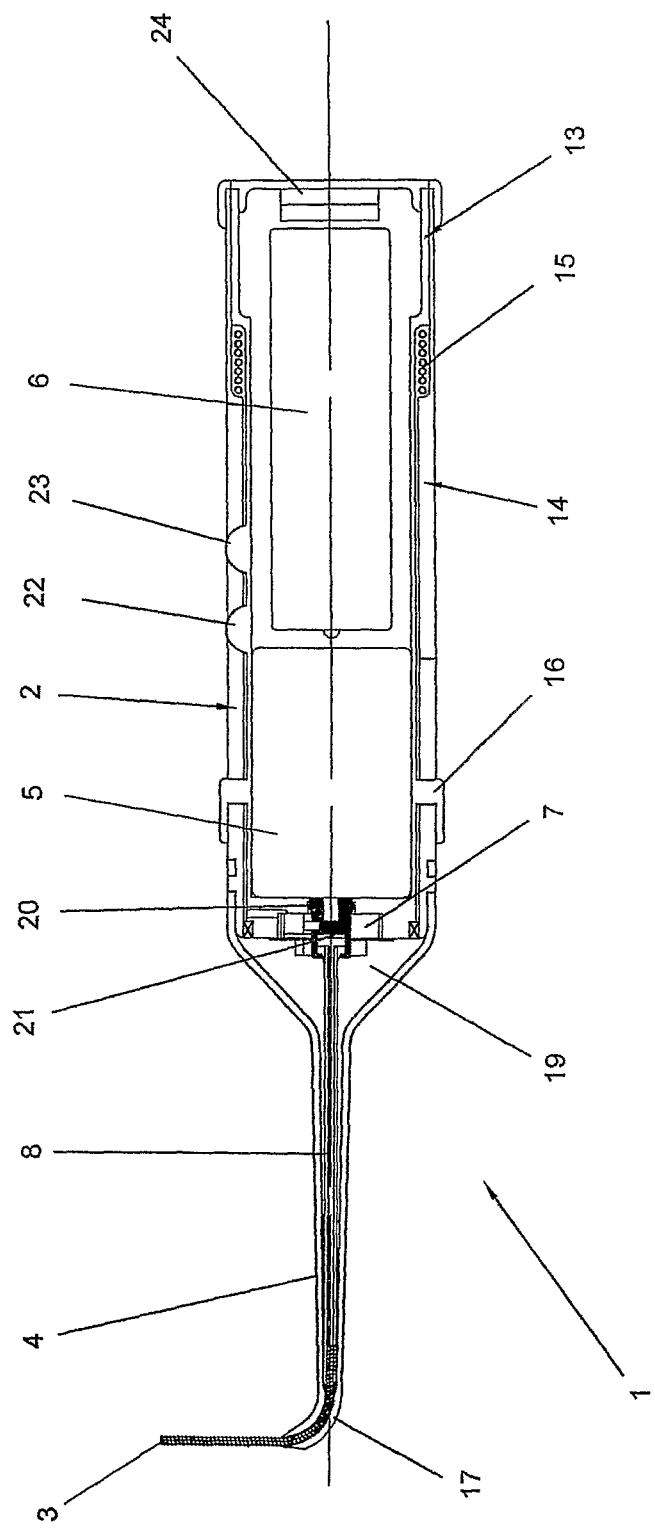
FIG. 1 is a schematic cross-sectional view of the teeth cleaning apparatus according to the invention, with the cleaning implement shown in an operative configuration.

According to the preferred embodiment of the invention, shown in FIG. 1, there is provided a teeth-cleaning apparatus 1 comprising an elongate housing 2 and a cylindrical cleaning implement 3 that is laterally supported within tubular support portion 4 at the front of the housing. Housing 2 includes the entire driving mechanism of apparatus 1, including electrical motor 5 and battery 6, as well as elements with additional functions, such as pump 7.

Figure 8:
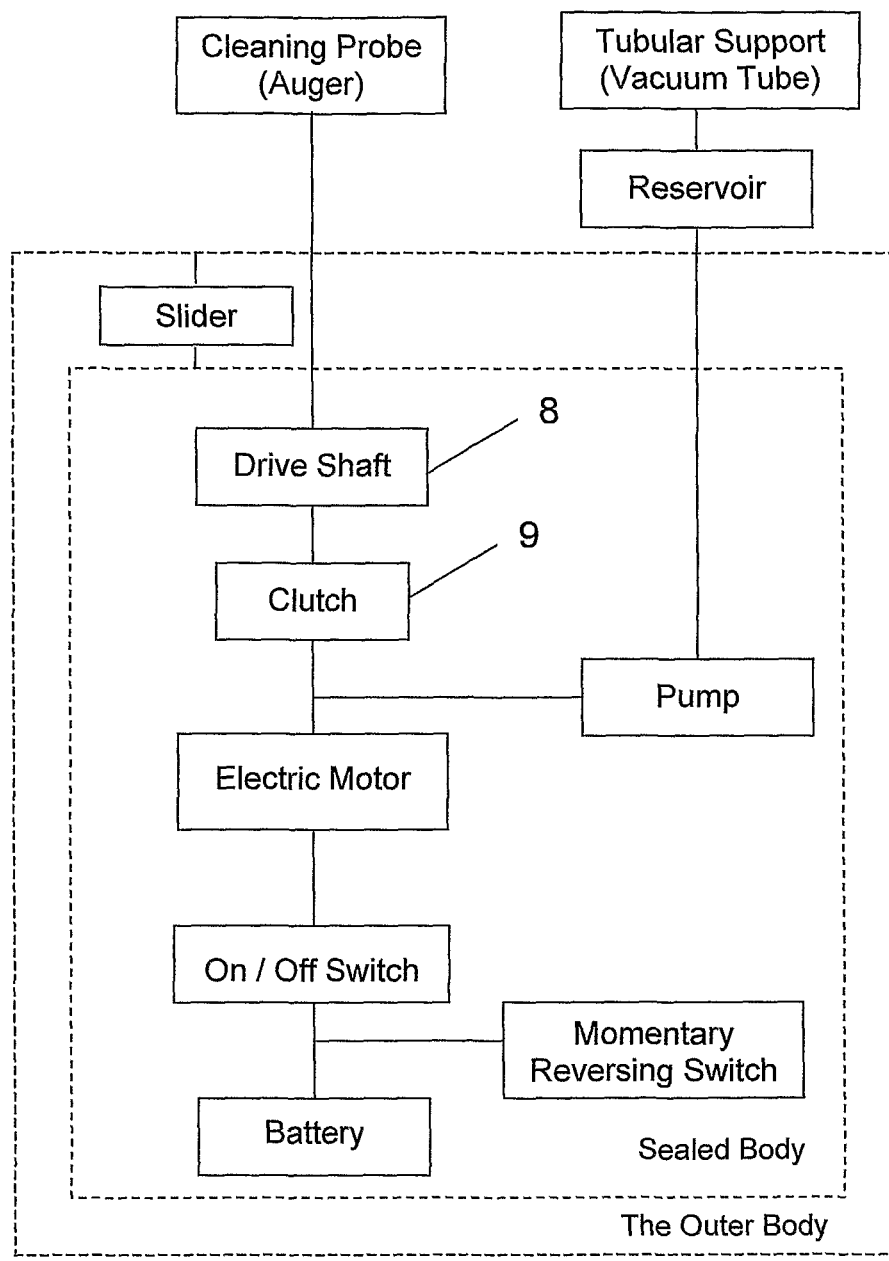
FIG. 8 is schematic functional diagram of the apparatus of FIG. 1.

Electric motor 5 is configured to rotate drive shaft 8 in both directions. Drive shaft 8 then transfers the rotational movement to cleaning implement 3. Clutch 9, schematically shown in FIG. 8, is arranged between motor 5 and drive shaft 8 to facilitate disengagement of drive shaft 8 from motor 5, in case of jamming of implement 3 in the interproximal space. In an alternative embodiment, clutch 9 can be located between drive shaft 8 and cleaning implement 3. Pump 7 is drivingly engaged with an additional shaft, not shown, that connects electric motor 5 to clutch 9.

FIGS. 3A to 7B show various embodiments of implement 3. The cleaning implement 3 of FIGS. 3A and 3B is of composite structure and includes a resilient support shaft 10 and a flexible continuous helical thread 11. Shaft 10 can be made of rigid but bendable plastic, while thread 11 can be made of flexible rubber, the different materials accommodating the different mechanical requirements to the shaft and the thread. However, most of the implements have integral bodies. For example, the implement in FIGS. 4A and 4B is similar to that in FIGS. 3A and 3B, but is molded in one piece. While some of the implements have soft threads that are made of soft urethane or neoprene, others have much less resilient threads. One such example is the mid-sized implement with a buttress thread, shown in FIGS. 5A and 5B. The implement of FIGS. 6A and 6B has a very small diameter of less than 0.5 mm, and a shallow thread for strength. Finally, FIGS. 7A and 7B represent a hollow implement, configured to allow vacuum to be applied further into the interproximal space, via an opening at the tip, or along the body of shaft 10 of cleaning implement 3. In at least one embodiment, the thread 11 has a substantially constant diameter and substantially constant helix angle along the length of the support shaft 10. In at least one embodiment, the helix angle extends all the way to the free tip end of the thread 11. All probes have a common drive interface 12.

Notably, thread 11 is configured so that, when presented between a pair of adjacent teeth, rotating cleaning implement 3, instead of having to be pushed, threads itself into the interproximal space between the teeth and extracts interproximal debris. This functionality is related to the auger-like structure of the thread defined by the particular helix angle. If the helix angle is defined with respect to a cross-sectional plane perpendicular to shaft 10 of implement 3, it is essential that the helix angle is small, usually in the range of one to sixty degrees. The most advantageous range, however, is considered to be the range from one to twenty degrees. It is clear that for large helix angles, close to ninety degrees, the engagement thread would approximate fluted profile and would easily jam in the narrow interproximal spaces. If the angle is too small, jamming will be avoided, but the self-threading functionality and the associated cleaning efficiency of the implement will be substantially reduced.

The electromechanical structure and functionality of the apparatus of the preferred embodiment are indicated in FIGS. 1 and 8. Apart from being drivingly rotated by motor 5, cleaning implement 3 is axially movable between a retracted configuration, wherein the implement is enclosed in tubular support portion 4 of the housing, and an operative configuration, shown in FIGS. 1 and 2, wherein the implement extends, at least partially, outside the housing so as to be applied in the interproximal space of a user for extracting debris. The operative configuration is shown in FIGS. 1 and 2.

The axial movement of implement 3 is facilitated by the housing being subdivided into a rear portion 13, including the driving mechanism, and a front portion 14, including tubular support portion 4 that houses and laterally supports cleaning implement 3. The rear portion 13 and the front portion 14 are telescopically engaged and are axially movable with respect to each other. In addition, spring 15 resiliently biases front portion 14 away from rear portion 13. The arrangement is such that, to effect the operative configuration of cleaning implement 3, one uses sliders 16 to push front portion 14 towards rear portion 13. Releasing the pressure on front portion 14 allows the bias to move the two portions apart and to bring implement 3 into the retracted configuration. Once implement 3 is withdrawn, the user may decide to turn off the entire device. Alternatively, the user may decide to continue the cleaning process using vacuum provided by pump 7, as will be described in some of the following paragraphs.

Supporting portion 4 includes a curved portion 17, which allows the tip of the implement to be supportingly introduced into the interproximal space under an angle with respect to the axis of the cleaning apparatus. Implement 3 is supported until it enters the interproximal gap to prevent it from flailing prior to insertion. Apart from providing lateral support for implement 3, curved section 17 also forcibly changes the cleaning implement's axis of rotation along its length. The fact that implement 3 can be advanced whilst the apparatus is operated allows access to restricted areas, such as the interproximal spaces of the back teeth. This makes the device convenient to use. At the same time, the dynamic modes of rotation and axial movement of cleaning implement 3, relative to the tubular support portion 4, as indicated by arrows in FIG. 2, may be independent of each other.

As mentioned above, apparatus 1 further includes a pump 7 arranged to provide vacuum. The created vacuum is applied via curved portion 17 of elongate tubular support portion 4, in the interproximal space adjacent cleaning implement 3, to facilitate extraction of debris. It should be noted that vacuum can be applied not only during the operation of implement 3, but also when implement 3 is in a retracted configuration. The vacuum can also be applied via one or more openings on the tip or along the shaft of any hollow implement, such as the implement shown in FIGS. 7A and 7B.

In this preferred embodiment, the debris is sucked into the housing and accumulated in a dedicated cavity 19. From here the debris is removed manually or is flushed out by way of vacuum created by pump 7. A system where the debris is directly flushed out, without being initially stored in the housing of the apparatus, can also be envisaged. Pump 7 can be of Racine or vane type. Using a vane type vacuum pump is recommended, since it produces a low-pressure pulse, around 50 Hz, which is ideal for loosening and removing impacted debris. Pump 7 can also be used for blowing air into the interproximal space.

We will now discuss some further specifics of the mechanical interaction between the various elements in apparatus 1. As shown in FIG. 1, tubular support portion 4 is removably attached to front body 14. Drive shaft 8 facilitates both the rotation and the axial translation of cleaning implement 3 through tubular support portion 4. Shaft 8 has provisions for attachment to cleaning implement 3 at one end and to coupling 20 at the other. Coupling 20 rotationally couples drive shaft 8 to drive motor 5 via a friction spring washer 21, thus providing limited torque to drive shaft 8 whilst restricting axial movement between drive shaft 8 and motor 5. The coupling 20 is firmly attached to the additional drive shaft of motor 5. Coupling 20 also provides rotational drive to the pump 7, to which it is removably attached, to facilitate easy cleaning.

Battery 6 is provided as a power source. An on/off switch 22 electrically connects battery 8 to motor 5, when required. Sprung reversing switch 23 facilitates the reverse rotation and the extraction of cleaning implement 3. The on/off switch 22 may also be used to set the speed of rotation of the cleaning implement by means of a control circuit. In the case of a rechargeable battery 6 being used a charging circuit and apparatus 24 may be provided.

In operation, the device is switched on and cleaning implement 3 is set to rotate at a suitable speed. The tip of the tubular support portion 4 is positioned at the entrance to an interproximal space where the rotating cleaning implement 3 is manually advanced from the tubular support. The implement threads itself into the interproximal space and starts extracting debris in an auger-like manner. Apart from extraction of debris, the implement removes the accumulated bio-film from the adjacent teeth. Should the cleaning implement jam, reversing switch 23 is used to reverse cleaning implement 3 out of the respective interdental space. The self-threading functionality of the implement and the constant peripheral support offered by the tubular support portion, when the implement is not in operation, allows for a much finer cleaning implement to be employed. Pump 7 augments the debris extraction process by sucking or blowing down the support tube. The cleaning implement, the tubular support portion, as well as any other parts of the apparatus 1, may be readily detachable from the telescopic body for cleaning and replacement.

It should be noted that components of the invention may be formed of metal, synthetic polymers or any other materials that provide the invention with desired properties such as rigidity and flexibility.

It is obvious from the above description that the apparatus of the preferred embodiment of the invention offers a reliable and efficient way for interproximal cleaning and removal of bio-film from user's teeth.

Although only one preferred embodiment has been described in detail, it should be understood that various changes, substitutions and alterations might be made herein by one ordinarily skilled in the art without departing from the spirit or scope of the present invention.

For example, the axial movement of the implement, provided in the preferred embodiment by the relative movement of front and rear portion of the housing, may be facilitated by other mechanical driving arrangements. Thus, in another embodiment, the cleaning implement's linear movement relative to the tubular support may be controlled by the cleaning implement's rotating mechanism. Also, a reservoir that is externally attachable to the housing may be provided to collect debris augured down the tubular support by the cleaning implement. In addition, it should be clear that, instead of being disposed along the length of the entire shaft, as shown in FIG. 2, the helical thread may be disposed on only on a portion of this length.

The invention claimed is:

1. Teeth cleaning apparatus comprising:
   an interproximal cleaning implement having:
   an elongate resilient support shaft having a fixed and free tip end portion;
   a continuous helical engagement thread formed around the support shaft, the thread being flexible, extending to the free tip end portion of the support shaft, and having a helix angle between 1 and 20 degrees at the free tip end portion, said helix angle being with respect to a plane transverse to a longitudinal axis of the implement; and
   a drive interface at one end of the support shaft for connecting the cleaning implement to a rotatable drive shaft,
   wherein, in use, when the tip of the cleaning implement is presented between a pair of adjacent teeth, the helical engagement thread causes the rotating cleaning implement to thread itself into an interproximal space and extracts interproximal debris.

2. Teeth cleaning apparatus according to claim 1, the apparatus further comprising an elongate housing and an electronic driving mechanism disposed in the housing, wherein the cleaning implement is, at least partially, laterally supported within the housing, drivingly rotated by the driving mechanism and axially movable between a retracted configuration, wherein the implement is enclosed in the housing, and an operative configuration, wherein the free end of the implement extends, at least partially, outside the housing.

3. Teeth cleaning apparatus according to claim 2, wherein the apparatus further comprises a pump for providing vacuum in the interproximal space to facilitate extraction of debris, the extracted debris being then flushed out of the cleaning apparatus or transferred to a dedicated storage space.

4. Teeth cleaning apparatus according to claim 3, wherein the shaft of the cleaning implement is hollow to facilitate applying of vacuum and extracting interproximal debris through an opening in the shaft.

5. Teeth cleaning apparatus according to claim 3, the driving mechanism comprising:
   an electric motor for drivingly rotating the cleaning implement;
   a first drive shaft arranged for engaging with a drive interface at the fixed end of the cleaning implement and the motor so as to transfer the rotational movement from the motor to the implement;
   a clutch arranged between the motor and the first drive shaft, the clutch being arranged to facilitate disengagement of the first drive shaft from the motor in case of jamming of the implement; and
   a second shaft arranged for engaging the electric motor to the clutch;
   wherein the second shaft is drivingly engaged with the pump.

6. Teeth cleaning apparatus according to claim 2, the housing comprising a rear portion, including the driving mechanism, and a front portion, including an elongate tubular support portion for housing and laterally supporting the cleaning implement, the rear and the front portions being axially movable with respect to each other, wherein moving the front portion towards the rear portion effects the operative configuration of the cleaning implement, and moving of the front portion away from the rear portion effects the retracted configuration of the cleaning implement.

7. Teeth cleaning apparatus according to claim 6, wherein the tubular support portion includes a curved portion to allow the tip of the implement to be introduced into the interproximal space under an angle with respect to the axis of the cleaning apparatus.

8. Teeth cleaning apparatus according to claim 7, wherein the angle in the curved portion is 90 degrees.

9. Teeth cleaning apparatus according to claim 6, wherein the front portion is resiliently biased away from the rear portion, the apparatus being configured such that pushing the front portion towards the rear portion effects the operative configuration of the cleaning implement, while releasing of the front portion allows the bias to bring the implement into the retracted configuration.

10. Teeth cleaning apparatus according to claim 1, wherein the support shaft and the engagement thread of the cleaning implement are of integral one-piece construction.

11. Teeth cleaning apparatus according to claim 1, wherein said engagement thread has a constant diameter along a length of the support shaft.

12. Teeth cleaning apparatus according to claim 11, wherein said engagement thread has a constant helix angle along the length of the support shaft.

13. Teeth cleaning apparatus comprising:
an elongate housing;
a driving mechanism disposed in the housing; and
an interproximal cleaning implement being, at least partially, laterally supported within the housing, the cleaning implement comprising:
a resilient support shaft;
a continuous helical engagement thread formed around the support shaft, the thread being flexible, extending to the free tip end portion of the support shaft, and having a helix angle between 1 and 20 degrees at the free tip end portion, said helix angle being with respect to a plane transverse to a longitudinal axis of the implement; and
a drive interface at one end of the support shaft for connecting the cleaning implement to a rotatable drive shaft,
wherein the cleaning implement is axially movable between a retracted configuration, wherein the implement is enclosed in the housing, and an operative configuration, wherein the implement extends, at least partially, outside the housing, and
wherein, in use, when presented between a pair of adjacent teeth, the helical engagement thread causes the rotating cleaning implement to thread itself into an interproximal space and extracts interproximal debris.

14. Teeth cleaning apparatus according to claim 13, wherein said engagement thread has a constant diameter along a length of the support shaft.

15. Teeth cleaning apparatus according to claim 14, wherein said engagement thread has a constant helix angle along the length of the support shaft.

* * * * *